United States Patent [19]

Schoenberg

[11] 4,168,302
[45] Sep. 18, 1979

[54] HAIR CONDITIONING COMPOSITIONS CONTAINING A NON-IRRITATING CATIONIC SURFACTANT

[75] Inventor: Thomas G. Schoenberg, Des Plaines, Ill.

[73] Assignee: The Richardson Company, Des Plaines, Ill.

[21] Appl. No.: 891,921

[22] Filed: Mar. 30, 1978

Related U.S. Application Data

[62] Division of Ser. No. 671,314, Mar. 29, 1976, abandoned.

[51] Int. Cl.$^2$ .............................................. A61K 7/06
[52] U.S. Cl. .............................. 424/70; 252/DIG. 13; 252/542
[58] Field of Search .................. 424/70; 260/404.5 Q; 252/DIG. 13, 542

[56] References Cited

U.S. PATENT DOCUMENTS

| | | | |
|---|---|---|---|
| B 438,048 | 3/1976 | Fogel et al. | 424/70 |
| 2,268,395 | 12/1941 | Henke et al. | 260/404.5 Q |
| 2,459,062 | 1/1949 | Cook et al. | 260/404.5 Q |
| 2,589,674 | 3/1952 | Cook et al. | 260/404.5 Q |
| 2,626,876 | 1/1953 | Carnes | 260/404.5 Q |
| 2,742,464 | 4/1956 | Koebner et al. | 260/247.2 |
| 2,950,255 | 8/1960 | Goff | 424/70 X |
| 2,983,650 | 5/1961 | Rubin | 424/47 |
| 3,082,227 | 3/1963 | Sherr | 260/404.5 Q |
| 3,144,391 | 8/1964 | Goff | 424/71 X |
| 3,322,676 | 5/1967 | Hiestand | 424/70 X |
| 3,959,461 | 5/1976 | Bailey et al. | 424/70 |

FOREIGN PATENT DOCUMENTS

353127  5/1961  Switzerland ............................. 424/71

*Primary Examiner*—James O. Thomas, Jr.
*Assistant Examiner*—Vera C. Clarke
*Attorney, Agent, or Firm*—Lockwood, Dewey, Alex & Cummings

[57] ABSTRACT

Cationic surfactants are provided which are useful alone as the active compounds in creme hair rinse and in conjunction with anionic surfactants in other hair conditioning preparations based on anionic-cationic surfactant systems. Such cationic surfactants are non-irritating to the eyes and are compatible with the other conventional ingredients used in hair conditioning preparations. These cationic surfactants are also compatible with anionic surfactants without objectionably reducing or otherwise interfering with the foam normally formed by the anionic surfactants in hair conditioning preparations. Useful cationic surfactants of the present invention have the following general formula:

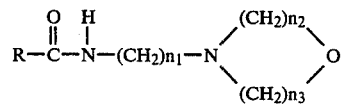

wherein

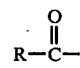

is a fatty acid group containing from 6 to 20 carbon atoms, and $n_1$, $n_2$ and $n_3$ are the same or different integers not exceeding 3. Two cationic surfactants of the invention presently preferred are: isostearylamidopropylmorpholine lactate and stearylamidopropylmorpholine lactate.

7 Claims, No Drawings

HAIR CONDITIONING COMPOSITIONS CONTAINING A NON-IRRITATING CATIONIC SURFACTANT

This is a division of application Ser. No. 671,314, filed Mar. 29, 1976, now abandoned.

BACKGROUND OF THE INVENTION

This invention relates to novel cationic surfactants which are non-irritating to the eyes and therefore particularly useful in preparing new and improved hair conditioning preparations. These cationic surfactants may be used alone in certain hair conditioning preparations, e.g. creme rinses. They are also useful in other hair conditioning preparations, e.g. shampoos, based on anionic-cationic surfactant systems. In order to be highly useful in anionic-cationic surfactant systems in hair conditioning preparations the cationic surfactants must not only be non-irritating to the eyes but also compatible in adequate proportions with the anionic surfactant constituents without objectionably reducing the foam normally produced by the latter. Cationic surfactants do not as a class generally possess this particular combination of properties. For example, while the quarternary compound, stearyldimethylbenzylammonium chloride, has been used as a cationic surfactant in hair conditioning preparations, it is irritating to the eyes. Another cationic surfactant which is more closely related to the non-irritant sub-class thereof provided by and found useful in accordance with the present invention, but which exhibits excessive eye irritating properties, is stearylamidopropyldimethylamine lactate. The sub-class of cationic surfactants useful according to the present invention have the following general formula:

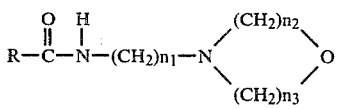

wherein

is a fatty acid group containing from 6 to 20 carbon atoms, and $n_1$, $n_2$ and $n_3$ are the same or different integers not exceeding 3.

Accordingly, the object of the invention, generally stated, is the provision of cationic surfactants which are non-irritating to the eyes and, therefore, useful in hair conditioning preparations wherein they are compatible with other ingredients conventionally used in such preparations.

An important object of the invention is the provision of cationic surfactants which are particularly suitable for use as the cationic portion of anionic-cationic systems in hair conditioning preparations since these cationic surfactants are not only non-irritating to the eyes but also compatible with the anionic surfactant portion without adversely depressing foam formation.

Another important object of the invention is the provision of new and improved hair conditioning preparations based on anionic-cationic surfactant systems containing cationic surfactant portions provided by the invention.

The cationic surfactants of the present invention may be produced from available raw materials by known processes in known commercial equipment and may be readily incorporated in hair conditioning preparations in accordance with known formulating procedures and techniques. In such preparations the cationic surfactants of the present invention serve to improve the manageability of the hair, soften the hair and reduce static charges thereon, and facilitate and improve its combing properties. In the production of the useful cationic surfactants, the selected fatty acid and difunctional amine are condensed to the amido-amine which in turn is neutralized in aqueous solution with a selected acid having an innocuous anion. Useful fatty acids are those containing from 8 to 20 carbon atoms and are illustrated by caproic, caprylic, capric, lauric, myristic, palmitic, oleic, linoleic, stearic and isostearic acids. Commercial grades of these fatty acids may be used including mixtures thereof such as found in natural products, e.g. coconut fatty acids. While both saturated and olefinically unsaturated fatty acids may be used, the saturated acids are preferred for their excellent color and oxidative stability. The difunctional amines useful for condensation with the fatty acids include amines of the following structures:

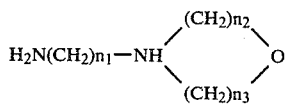

and in particular N-aminopropylmorpholine. The amido-amine condensation products are neutralized to form amine salts with either organic or inorganic acids. The useful acids, whether inorganic or organic must be characterized by an innocuous anion. The following lower molecular weight aliphatic carboxylic acids may be used: acetic, propionic, lactic, citric, tartaric, formic, dimethylolpropionic, ethylene diamine tetra acetic succinic, maleic and fumaric. Mineral or inorganic acids that may be used include: hydrochloric, nitric, sulphuric, and phosphoric acid. Other acids having innocuous anions that may be used include toluene sulfonic acid, dodecyl benzene sulfonic acid and benzoic acid.

For a more complete understanding of the nature and scope of the invention, reference may now be had to the following detailed description thereof wherein preferred working examples are set forth along with certain comparative test results.

Tests for compatibility, foam depression and eye irritation were made utilizing cationic surfactants of the sub-class or group provided by and found useful in accordance with the present invention, and for comparison, two cationic surfactants not found useful in accordance therewith. Two different types of anionic surfactants were also employed in conducting the tests. The cationic surfactants found useful in accordance with the present invention that were utilized in the tests were as follows:

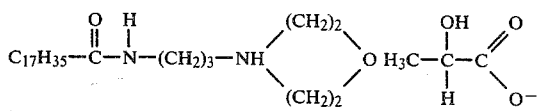

The two cationic surfactants that were also used for comparison purposes, but not within the group of sub-class found useful in accordance with the present invention, were the following:

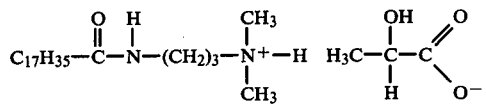

Stearylamidopropyldimethylamine Lactate (SDML). This compound is an eye irritant but otherwise useful in hair conditioning preparations.

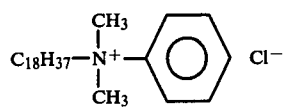

Stearyldimethylbenzylammonium Chloride (SDBAC). This quarternary compound is an eye irritant and not adequately compatible in anionic-cationic surfactant systems.

The two anionic surfactants that were used in conducting the tests were:
Triethanolamine lauryl sulfate (TEALS)
Sodium lauryl ether sulfate (NaLES)

COMPATIBILITY

Absence or presence of cloudiness at room temperature (25° C.) was used as the criterion in determining compatibility of the anionic-cationic surfactant systems tested. All solutions, both cationic and anionic, were adjusted to 10.0% active (i.e. solids content of the surfactant in the solution) and pH 6.0. The solutions were blended at various ratios to obtain the transition points between cloudiness and clarity. The following tables contain the maximum concentrations of 10.0% active pH 6.0 solutions of the four cationic surfactants that were compatible with the two anionic surfactants, respectively:

TABLE 1

| Cationic Surfactant | % Concentration |
|---|---|
| (Compatability in TEALS) | |
| SDML | 34.1 |
| SMOL | 32.5 |
| SDBAC | 17.5 |

TABLE 2

| Cationic Surfactant | % Concentration |
|---|---|
| (Compatibility in NaLES) | |
| SDML | 18.0 |
| SMOL | 20.1 |
| SDBAC | 5.0 |

These data clearly show SDBAC to be least compatible.

FOAM DEPRESSION

Foam depression measurements were made by comparing the relative foam properties of 3:1 and 1:1 ratio of the anionic to cationic surfactants. The Ross-Miles Foam Test, Standard Test Method for Foaming Properties of Surface Active Agents, ASTM D1173, was used. All solutions totaled 0.2% active in 138 ppm hardness water at 25° C. Only initial foam heights were compared since after five minutes it was observed that all foam heights showed little, if any, reduction. In the ratio of 3 anionic to 1 cationic with the anionic surfactant being TEALS it was found that SDML had no appreciable foam depressing effect. SMOL depressed the foam height of the TEALS approximately 16.3% while SDBAC depressed the foam height approximately 31.5%. When the ratio of anionic to cationic was 1:1, SDML and SMOL each depressed the foam height approximately 83% while SDBAC depressed it approximately 92%.

When the foam depression test was carried out using NaLES as the anionic surfactant, it was found that in the 3:1 anionic to cationic comparisons, SDML depressed the foam approximately 16% while SMOL and SDBAC each depressed the foam approximately 22%. With a 1:1 anionic to cationic ratio SDML and SMOL each depressed the foam approximately 83% while SDBAC depressed it approximately 92%.

EYE IRRITATION

In order to compare relative irritation properties of the cationic surfactants tested all solutions were adjusted to 4.0% active and pH 4.5. The Draize irritation test was then run on each solution (Draize J. H. et al, Journal of Pharmacology and Experimental Therapeutics, Vol. 82, 1974, p. 377) as modified (Sec. 191.12, Federal Hazardous Substances Labeling Act Regulations Guide for Grading Eye Irritation). Albino rabbits were used and 0.1 millileter of each cationic surfactant was instilled in the right eye of each rabbit while the left eye thereof remained untreated to serve as a control. Observations for ocular lesions were made on the rabbits' eyes after 24, 48 and 72 hours. At these intervals the extent and degree of irritation were graded according to the following system:

| Cornea | |
|---|---|
| No ulceration or opacity | 0 |
| Scattered or diffuse areas of opacity (other than slight dulling of normal luster), details of iris clearly visible | 1 |
| Easily discernible translucent areas, details of iris slightly obscured | 2 |
| Nacreous areas, no details of iris visible, size of pupil barely discernible | 3 |
| Complete orneal opacity, iris not discernible | 4 |
| Iris | |
| Normal | 0 |
| Markedly deepened folds, congestion, swelling, moderate circumcorned injection (any of these or combination thereof), iris still reacting to light (sluggish reaction is positive) | 1 |
| No reaction to light, hemorrage, gross destruction (any or all of these) | 2 |
| Conjunctivea | |
| Redness (refers to palpebral and bulbar conjunctivea excluding cornea and iris) | |
| Vessels normal | 0 |
| Some vessels definitely injected | 1 |
| Diffuse, crimson red, individual vessels not easily discernible | 2 |
| Diffuse, beefy red | 3 |

| Chemosis | |
|---|---|
| No swelling | 0 |
| Any swelling above normal (includes nicitating membrane) | 1 |
| Obvious swelling with partial eversion of lids | 2 |
| Swelling with lids about half closed | 3 |
| Swelling with lids more than half closed | 4 |

The results of these eye irritation tests are summarized in the following table:

TABLE 3

Comparative eye irritation scores for SDML, SMOL, and SDBAC
(all tests were run at 4.0% active, pH 4.5)

| Hours after treatment | Rabbit No. 1 | | | Rabbit No. 2 | | | Rabbit No. 3 | | |
|---|---|---|---|---|---|---|---|---|---|
| | 24 | 48 | 72 | 24 | 48 | 72 | 24 | 48 | 72 |
| Stearylamidopropyldimethylamine Lactate (SDML) | | | | | | | | | |
| Cornea: | 2 | 2 | 2 | 2 | 2 | 2 | 2 | 2 | 2 |
| Iris: | 1 | 1 | 1 | 1 | 1 | 1 | 1 | 1 | 1 |
| Conjunctivea | | | | | | | | | |
| Erythema: | 2 | 2 | 2 | 2 | 3 | 3 | 2 | 2 | 2 |
| Chemosis: | 3 | 3 | 3 | 3 | 3 | 3 | 3 | 3 | 3 |
| Stearylamidopropylmorpholine Lactate (SMOL) | | | | | | | | | |
| Cornea: | 0 | 0 | 0 | 0 | 0 | 0 | 0 | 0 | 0 |
| Iris: | 0 | 0 | 0 | 0 | 0 | 0 | 0 | 0 | 0 |
| Conjunctivea | | | | | | | | | |
| Erythema: | 0 | 0 | 0 | 1 | 1 | 0 | 0 | 0 | 0 |
| Chemosis: | 0 | 0 | 0 | 0 | 0 | 0 | 0 | 0 | 0 |
| Stearyldimethylbenzylammonium Chloride (SDBAC) | | | | | | | | | |
| Cornea: | 2 | 2 | 2 | 2 | 2 | 2 | 2 | 2 | 2 |
| Iris: | 0 | 0 | 0 | 0 | 0 | 0 | 0 | 0 | 0 |
| Conjunctivea | | | | | | | | | |
| Erythema: | 2 | 1 | 1 | 2 | 1 | 1 | 2 | 1 | 1 |
| Chemosis: | 2 | 1 | 1 | 2 | 1 | 1 | 2 | 1 | 1 |

It is apparent from the foregoing table that at the level tested, SMOL is non-irritating, whereas, SDML and SDBAC, are severe eye irritants.

SPECIFIC FORMULATIONS

The following specific formulations will serve to illustrate hair conditioning preparations that may be prepared in accordance with the present invention using anionic-cationic surfactant systems of the type provided thereby.

| Low Viscosity Acid Shampoo | % by Weight |
|---|---|
| Triethanolamine lauryl sulfate (40.0%) | 35.0 |
| Cocoamidopropylbetaine (30.0%) | 10.0 |
| Stearylamidopropylmorpholine Lactate | 1.5 |
| Citric Acid to pH 4.0 | q.s. |
| Water, preservative, dye, perfume q.s. | 100.0 |

The isostearylamidoamine salts were found to have better compatibility and viscosity-building properties than the normal stearyl derivatives.

What is claimed as new is:

1. An aqueous hair conditioning composition having as the primary surfactant ingredients therein an anionic-cationic surfactant system and containing, an anionic surfactant, and an operative proportion of a cationic surfactant characterized by its being non-irritating to the eyes and compatible with said anionic surfactant without objectionable reduction of the foam normally produced by said anionic detergent and composed of an innocuous anion and a cation having the following structural formula:

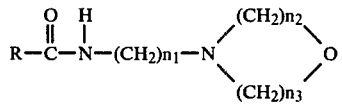

wherein

is a fatty acid group containing from 6 to 20 carbon atoms, $n_1$, $n_2$ and $n_3$ are the same or different integers not exceeding 3.

2. The composition of claim 1 wherein said innocuous anion is an inorganic anion selected from the group consisting of chloride and sulfate anions.

3. The composition of claim 1 wherein said innocuous anion is an organic anion selected from the group consisting of acetate, propionate, dimethylol propionate, glutamate, citrate, lactate, ethylenediaminetetraacetate, gluconate and maleate anions.

4. The composition of claim 1 wherein

is the fatty acid group of a fatty acid selected from the group consisting of caproic, caprylic, capric, lauric, myristic, palmitic, oleic, linoleic, stearic, and isostearic acids.

5. The composition of claim 1 wherein $n_1$ is 3 and $n_2$ and $n_3$ are each 2.

6. The composition as called for in claim 1 wherein the cationic surfactant is selected from the group consisting of isostearylamidopropylmorpholine lactate and stearylamidopropylmorpholine lactate.

7. The hair conditioning composition of claim 1 wherein the anionic surfactant is an alcohol sulfate.

UNITED STATES PATENT AND TRADEMARK OFFICE
CERTIFICATE OF CORRECTION

PATENT NO. : 4,168,302
DATED : September 18, 1979
INVENTOR(S) : Thomas G. Schoenberg It is certified that error appears in the above–identified patent and that said Letters Patent are hereby corrected as shown below:

Column 2, line 17, after "linoleic," insert --linolenic,--

Column 2, line 38, "of" should read --or--

Column 4, in the table under the heading "Cornea", line 11, "orneal" should read --corneal--

Column 4, in the table under the heading "Iris", line 3, "circumcorned" should read --circumcorneal--

Signed and Sealed this

Fifth Day of February 1980

[SEAL]

Attest:

Attesting Officer

SIDNEY A. DIAMOND

Commissioner of Patents and Trademarks